United States Patent [19]

Matsushita et al.

[11] Patent Number: 5,094,952
[45] Date of Patent: Mar. 10, 1992

[54] ASPARAGINYL ENDOPEPTIDASE, COMPOSITION AND USE THEREOF

[75] Inventors: Hideyuki Matsushita, Muko; Ikunoshin Kato, Uji; Yukichi Abe, Sapporo; Shin-ichi Ishii, Ichikawa, all of Japan

[73] Assignee: Takara Shuzo Co., Ltd., Kyoto, Japan

[21] Appl. No.: 527,729

[22] Filed: May 23, 1990

[30] Foreign Application Priority Data

Nov. 17, 1989 [JP] Japan ................................. 1-297450

[51] Int. Cl.$^5$ .................... C12N 9/48; C12N 9/78; C12N 9/80
[52] U.S. Cl. ........................... 435/212; 435/227; 435/228
[58] Field of Search ................ 435/68.1, 212, 227, 435/228

[56] References Cited

U.S. PATENT DOCUMENTS 3,929,756 12/1975 Leeman et al. .................. 530/327
4,086,136 4/1978 Isowa et al. ...................... 435/68.1
4,751,284 6/1988 Forssmann ....................... 530/324

OTHER PUBLICATIONS

Yoshida et al, *Characterization of an Apparently Lower . . .*, J. of Biol. Chem., vol. 263, No. 27, pp. 13848–13856.
Momand et al, *Rapid Degradation of D and C . . .*, Biochemistry, 26, pp. 7798–7805, 1987.
Stark et al, *The Killer Toxin of Kluyveromyces . . .*, EMBO Journal, vol. 5, No. 8, pp. 1995–2002, 1986.
Ishii et al., *An Asparaginyl Endopeptidase . . .*, J. Protein Chem., vol. 9, No. 3, pp. 294–295, 1990.

*Primary Examiner*—Douglas W. Robinson
*Assistant Examiner*—Michael V. Meller
*Attorney, Agent, or Firm*—Wenderoth, Lind & Ponack

[57] ABSTRACT

An asparaginyl endopeptidase which is specific for only an amide bond on the C-terminal side of an L-asparagine. Also disclosed is a method for the hydrolysis of an amide bond on the C-terminal side of an L-asparagine characterized by the use of an asparaginyl endopeptidase as well as a composition for use in the hydrolysis of an amide bond on the C-terminal side of an L-asparagine.

2 Claims, 2 Drawing Sheets

FIG. 1

```
  1
Lys-Val-Phe-Gly-Arg-Cys-Glu-Leu-Ala-Ala-Ala-Met-Lys-Arg-His-Gly-Leu-Asp-Asn-Tyr-
                      *                  10                                    20
 21
Arg-Gly-Tyr-Ser-Leu-Gly-Asn-Trp-Val-Cys-Ala-Ala-Lys-Phe-Glu-Ser-Asn-Phe-Asn-Thr-
                                30*                                            40
 41
Gln-Ala-Thr-Asn-Arg-Asn-Thr-Asp-Gly-Ser-Thr-Asp-Tyr-Gly-Ile-Leu-Gln-Ile-Asn-Ser-
                                       50                                      60
 61
Arg-Trp-Trp-Cys-Asn-Asp-Gly-Arg-Thr-Pro-Gly-Ser-Arg-Asn-Leu-Cys-Asn-Ile-Pro-Cys-
            *                          70                    *                 80*
 81
Ser-Ala-Leu-Leu-Ser-Ser-Asp-Ile-Thr-Ala-Ser-Val-Asn-Cys-Ala-Lys-Lys-Ile-Val-Ser-
                                       90          *                          100
101
Asp-Gly-Asn-Gly-Met-Asn-Ala-Trp-Val-Ala-Trp-Arg-Asn-Arg-Cys-Lys-Gly-Thr-Asp-Val-
                                      110                *                    120
121
Gln-Ala-Trp-Ile-Arg-Gly-Cys-Arg-Leu
                    *          128
```

Cys* : s-3-(trimethylammonio)propylcystein

5,094,952

ASPARAGINYL ENDOPEPTIDASE, COMPOSITION AND USE THEREOF

BACKGROUND OF THE INVENTION

1. Field of the Invention

This invention relates to a method for the hydrolysis of the amide bond on the C-terminal side of L-asparagine, by the use of a hydrolase which is specific for only the amide bond on the C-terminal side of L-asparagine contained in a compound having a peptide chain which has at least one amide bond on the C-terminal side of L-asparagine, to a reagent for use in such hydrolysis, and also to a novel asparaginyl endopeptidase which is of the same description as the above hydrolase.

2. Description of Related Art

Methods for the hydrolysis of peptide bonds only on the N-terminal side or the C-terminal side of a specific amino acid residue which is contained in a peptide chain, in which the recognition is selective and specific, are essential procedures for the analysis of protein structure and for the modification of proteins.

At the present, methods by which this purpose can be achieved have been established for the hydrolysis of the peptide bond on the C-terminal side of L-lysine, for the hydrolysis of the peptide bond on the N-terminal side of L-lysine, for the hydrolysis of the peptide bond on the C-terminal side of L-arginine, for the hydrolysis of the peptide bond on the C-terminal side of L-glutaminate and L-aspartic acid, for the hydrolysis of the peptide bond on the N-terminal side of L-aspartic acid, and for the hydrolysis of the peptide bond on the C-terminal side of L-proline, all of which are methods involving biochemistry. There are also methods which involve organic chemistry for the cleavage of the peptide bond on the C-terminal side of L-methionine, the cleavage of the peptide bond on the N-terminal side of L-cysteine, and the cleavage of the peptide bond on the C-terminal side of L-tryptophan.

In protein engineering, methods for the specific cleavage of a particular peptide bond of each of various amino acids are desired. However, there has been no method for the specific cleavage of amino acids other than those mentioned above.

SUMMARY OF THE INVENTION

The object of this invention is to provide a method and reagent for the hydrolysis of amide bonds on the C-terminal side of L-asparagine residues.

Briefly, this invention firstly, relates to a method for the hydrolysis of the amide bond on the C-terminal side of L-asparagine by a hydrolase which is selectively active for only the amide bond on the C-terminal side of L-asparagine contained in a compound having a peptide chain which has at least one amide bond on the C-terminal side of L-asparagine. Secondly, this invention relates to a reagent for use in the hydrolysis of the amide bond on the C-terminal side of L-asparagine, said reagent containing a protease which is selectively active for only the amide bond on the C-terminal side of L-asparagine contained in a compound having a peptide chain which has at least one amide bond on the C-terminal side of L-asparagine. Thirdly, this invention relates to a novel asparaginyl endopeptidase.

Based on the fact that there is L-asparagine at the C-terminal of lectins and stored proteins, in plant seeds, the inventors of this invention searched for a protease which would hydrolyze the amide bond on the C-terminal side of the L-asparagine in the peptide chains in plant seeds, and isolated and purified a protease which hydrolyzes only the amide bond on the C-terminal side of the L-asparagine in the peptide chains from the seeds of *Canavalia ensiformis*, thus accomplishing this invention. This invention has been completed by the establishment of a method for the preparation of this enzyme, by the investigation of its properties and by a study on use thereof. This invention will be explained in detail as follows.

Method for the Preparation of the Enzyme

The enzyme to be used in this invention can be prepared by, for example, the homogenization of commercially available jack bean meal in the presence of a suitable reduction agent in a buffer at pH 4–6, to solubilize this enzyme, after which centrifugation or the like is carried out to remove insoluble matter, followed by purification steps with the use of a variety of ion-exchange chromatography columns, gel filtration, etc., for increasing purity of the enzyme, and next the use of paramercuribenzoic acid (PMB), which is a specific inhibitor for this enzyme, immobilized to agarose in affinity chromatography, by which a single protein is obtained, which is the purified enzyme.

Although only one example of the enzyme and of the method for its preparation is given here, any enzyme which has the activity as defined in the claims can be used in the method for the hydrolysis and the reagent of this invention.

Assay of the Enzyme and Definition of Units

The substrate used in the assay of the enzyme is DNP-L-Pro-L-Glu-L-Ala-L-Asn-NH$_2$, where DNP is 2,4-dinitrophenyl. A reaction mixture containing this substrate at a concentration of 0.02 mM, 5 mM of dithiothreitol (DTT), 2 mM of ethylenediamine tetracetic acid (EDTA), the enzyme, and 0.002 mM of DNP-L-Ser as the internal standard in 20 mM acetate buffer (pH 5.0) is heated 10–20 minutes at 37° C. to proceed the reaction, and then formic acid is added to be a final concentration of 10% to stop the reaction. A portion of the reaction liquid is then analyzed by high-performance liquid chromatography (HPLC) with, for example, an ODS column, after which the activity of this enzyme can be calculated by the relative amount of DNP-L-Pro-L-Glu-L-Ala-L-Asn produced and the amount of DNP-L-Ser used as the internal standard. One unit of enzyme activity is defined as the amount of enzyme needed to produce 1 μmol of DNP-L-Pro-L-Glu-L-Ala-L-Asn in one minute.

Substrate Specificity of the Enzyme

The following were used as substrates for the enzyme at the substrate-to-enzyme ratio of 50:1 and reaction was conducted for 15 hours at 37° C. and pH 5.0: neurotensin, mastoparan, β-endorphin, parathyroid hormone (1–34), vasoactive intestinal peptide, peptide T, bombesin, oxidized insulin B chain, and physalamin. It was found that only the amide bond on the C-terminal side of the L-asparagine was hydrolyzed and no other peptide bonds were hydrolyzed. Table 1 shows the amino acid sequences of the synthetic peptides used as substrates and the location of the amide bond or bonds which were hydrolyzed.

TABLE 1

| Substrate | Amino acid sequence | Amide bond hydrolyzed |
|---|---|---|
| Neurotensin | Pyr—Leu—Tyr—Glu—Asn—Lys—Pro—Arg—Arg—Pro—Tyr—Ile—Leu | $\mathrm{Asn}\overset{5\ \ \ 6}{\longrightarrow}\mathrm{Lys}$ |
| Mastoparan | Ile—Asn—Leu—Lys—Ala—Leu—Ala—Ala—Leu—Ala—Lys—Lys—Ile—Leu—NH$_2$ | $\mathrm{Asn}\overset{2\ \ \ 3}{\longrightarrow}\mathrm{Leu}$ |
| β-Endorphin (human) | Tyr—Gly—Gly—Phe—Met—Thr—Ser—Glu—Lys—Ser—Gln—Thr—Pro—Leu—Val—Thr—Leu—Phe—Lys—Asn—Ala—Ile—Ile—Lys—Asn—Ala—Tyr—Lys—Lys—Gly—Glu | $\mathrm{Asn}\overset{20\ \ \ 21}{\longrightarrow}\mathrm{Ala}$ $\mathrm{Asn}\overset{25\ \ \ 26}{\longrightarrow}\mathrm{Ala}$ |
| Parathyroid hormone (human, 1-34) | Ser—Val—Ser—Glu—Ile—Gln—Leu—Met—His—Asn—Leu—Gly—Lys—His—Leu—Asn—Ser—Met—Glu—Arg—Val—Glu—Trp—Leu—Arg—Lys—Lys—Leu—Gln—Asp—Val—His—Asn—Phe | $\mathrm{Asn}\overset{10\ \ \ 11}{\longrightarrow}\mathrm{Leu}$ $\mathrm{Asn}\overset{16\ \ \ 17}{\longrightarrow}\mathrm{Ser}$ $\mathrm{Asn}\overset{33\ \ \ 34}{\longrightarrow}\mathrm{Phe}$ |
| Vasoactive intestinal peptide (human, porcine) | His—Ser—Asp—Ala—Val—Phe—Thr—Asp—Asn—Tyr—Thr—Arg—Leu—Arg—Lys—Gln—Met—Ala—Val—Lys—Lys—Tyr—Leu—Asn—Ser—Ile—Leu—Asn—NH$_2$ | $\mathrm{Asn}\overset{9\ \ \ 10}{\longrightarrow}\mathrm{Tyr}$ $\mathrm{Asn}\overset{24\ \ \ 25}{\longrightarrow}\mathrm{Ser}$ $\mathrm{Asn}\overset{28}{\longrightarrow}\mathrm{NH}_2$ |
| Peptide T | Ala—Ser—Thr—Thr—Thr—Asn—Tyr—Thr | $\mathrm{Asn}\overset{6\ \ \ 7}{\longrightarrow}\mathrm{Tyr}$ |
| Bombesin | Pyr—Gln—Arg—Leu—Gly—Asn—Gln—Trp—Ala—Val—Gly—His—Leu—Met—NH$_2$ | $\mathrm{Asn}\overset{6\ \ \ 7}{\longrightarrow}\mathrm{Gln}$ |
| Oxidized insulin B chain | Phe—Val—Asn—Gln—His—Leu—Cys—Gly—Ser—His—Leu—Val—Glu—Ala—Leu—Tyr—Leu—Val—Cys—Gly—Glu—Arg—Gly—Phe | $\mathrm{Asn}\overset{3\ \ \ 4}{\longrightarrow}\mathrm{Gln}$ |
| Physalamin | Pyr—Ala—Asp—Pro—Asn—Lys—Pro—Tyr—Gly—Leu—Met—NH$_2$ | $\mathrm{Asn}\overset{5\ \ \ 6}{\longrightarrow}\mathrm{Lys}$ |

Other Enzymatic and Biochemical Properties of This Enzyme

1) Molecular weight 32,200 as found by SDS-polyacrylamide electrophoresis on 12% gel.

26,550 as found by gel permeation on Tosoh G3000SW.

2) Optimal pH—pH 6.0-7.0.

The reaction was with DNP-L-Pro-L-Glu-L-Ala-L-Asn-NH$_2$ as substrate in the presence of 5 mM DTT in buffer at different pH for 20 minutes at 37° C.

3) Optimum temperature—Vicinity of 45° C.

The reaction was with DNP-L-Pro-L-Glu-L-Ala-L-Asn-NH$_2$ as substrate in the presence of 5 mM DTT in buffer at pH 5.0 at different temperatures for 20 minutes.

4) Stability against pH—Stable at pH 4.5-6.5.

The remaining activity was assayed after 6 hours of incubation of the enzyme in buffer containing 1 mM DTT at different pH at 37° C.

5) Stability against heat

When the enzyme was heated at 55° C. for 15 minutes in buffer containing 1 mM DTT at pH 5.0, enzyme activity was not lost. When the enzyme was heated at 65° C. for 15 minutes, 90% or more of the enzyme activity was lost.

BRIEF DESCRIPTION OF THE FIGURES

The invention will be further explained by the following Examples and by referring partly to the accompanying drawings wherein:

FIG. 1 shows the amino acid sequence of the commercial soluble reduced lysozyme used as the substrate in Example 2;

DESCRIPTION OF THE PREFERRED EMBODIMENTS

EXAMPLE 1

Figure 2:
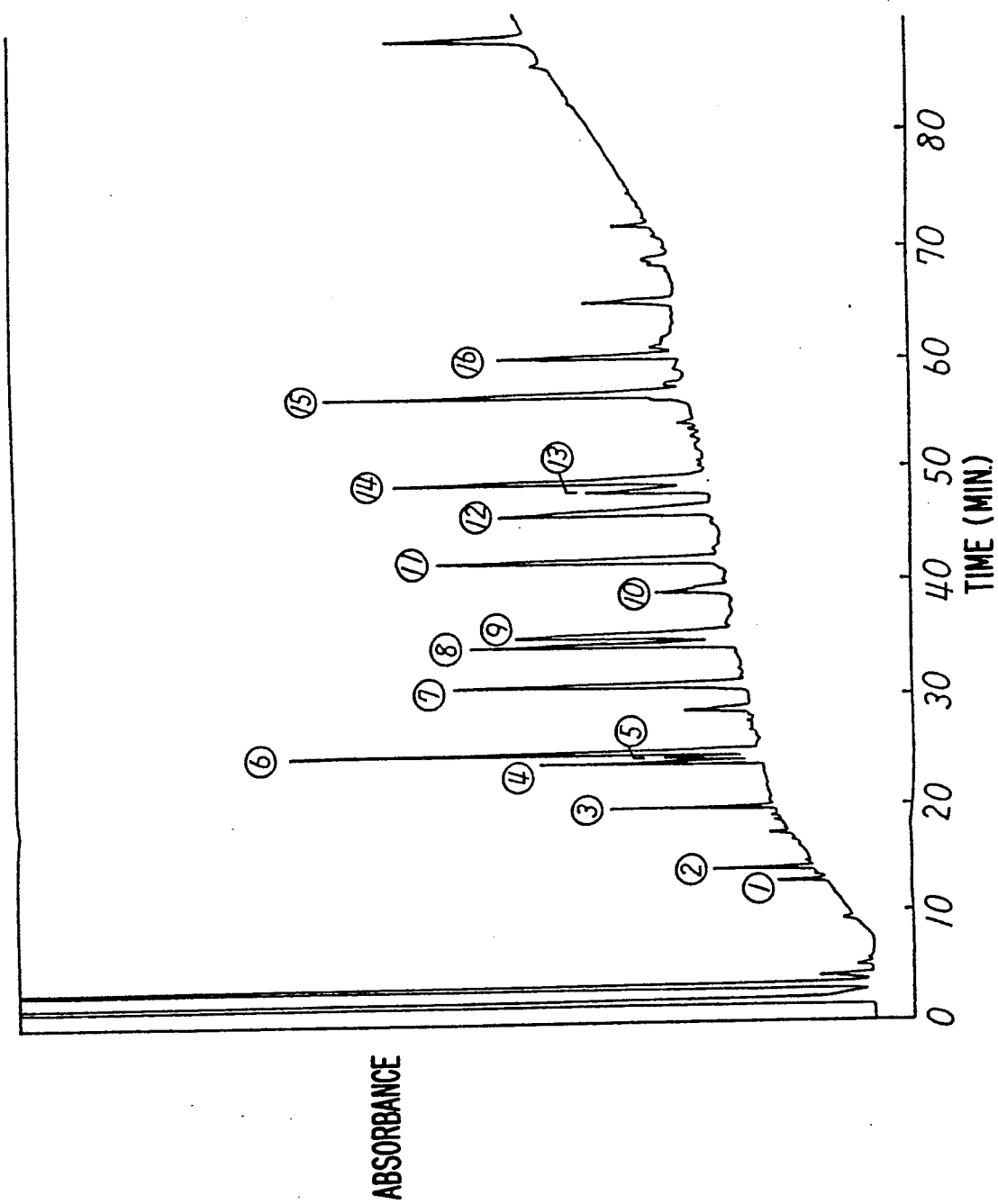
FIG. 2 shows the elution profile of fractions by reversed-phase HPLC with the use of a C4 column when a digest of soluble reduced lysozyme obtained by treatment with the enzyme of this invention is put on the column, in which the X-axis is time (min) and the Y-axis (0.32 of the original scale) is the absorbance at 215 nm.

First, 500 g of commercially available jack bean meal (Sigma) was homogenized in acetate buffer (pH 5.0) containing 1 mM DTT and 1 mM EDTA, and the homogenate was centrifuged. The supernatant obtained was dialyzed in the same buffer, after which the formed precipitate was removed by centrifugation, and the supernatant was treated by ion-exchange chromatography on a column of SP-Toyopearl 650M (Tosoh Corp.). The substance adsorbed to the SP-Toyopearl 650M column was eluted with 0.5M sodium chloride, and the active fraction was precipitated with 60% saturated ammonium sulfate and dialyzed against the same buffer as before. Then the dialysate was treated by affinity chromatography on an affinity column of agarose on which PMB had been immobilized. The active fraction eluted from this column with 0.5M sodium chloride was dialyzed against the same buffer, and then treated by affinity chromatography on a Leu-ArgH column (Organo), with collection of the active fraction which was not adsorbed on the column. The active fraction was concentrated in a membrane filter with a molecular weight cut-off of 10,000, and the concentrate was treated by gel filtration on Toyopearl HW-55S (Tosoh). The amount of purified enzyme thus obtained was 2.6 mg, and the activity was 180 mU. The protein was a single protein, judging from the results of electrophoresis on SDS-polyacrylamide and reverse-phase chromatography with a C4 column.

EXAMPLE 2

The enzyme obtained in Example 1 was used for the limited hydrolysis of commercially available soluble reduced lysozyme (Seikagaku Kogyo). The reaction was in 20 mM sodium acetate buffer (pH 5.0) containing 10 mM DTT and 1 mM EDTA; the concentration of the substrate was 0.2 mM and that of the enzyme was 0.004 mM; the reaction was conducted for 15 hours at 37° C. The reaction was stopped by the addition of formic acid to a final concentration of 10%. The peptide fragments produced were separated by reversed-phase chromatography on a C4 column (Waters; μBondasphere 3.9×150 mm), and the amino acid composition and the amino acid sequence of each fragment were analyzed. The soluble reduced lysozyme had the amino acid sequence shown in FIG. 1. The results of the reversed-phase chromatography on a C4 column are shown in FIG. 2, and the amino acid sequence of each fragment obtained are shown in Table 2.

TABLE 2

| Peak numbers in FIG. 2 | Amino acid sequence of peptide fragment |
|---|---|
| ① | $^{38}$Phe—Asn—Thr—Gln—Ala—Thr—Asn$^{44}$ |
| ② | $^{94}$Cys—Ala—Lys—Lys—Ile—Val—Ser—Asp—Gly—Asn$^{103}$ |
| ③ | $^{20}$Tyr—Arg—Gly—Tyr—Ser—Leu—Gly—Asn$^{27}$ |
| ④ | $^{28}$Trp—Val—Cys—Ala—Ala—Lys—Phe—Glu—Ser—Asn$^{37}$ |
| ⑤ | $^{66}$Asp—Gly—Arg—Thr—Pro—Gly—Ser—Arg—Asn$^{74}$ |
| ⑥ | $^{60}$Ser—Arg—Trp—Trp—Cys—Asn$^{65}$ |
| ⑦ | $^{107}$Ala—Trp—Val—Ala—Trp—Arg—Asn$^{113}$ |
| ⑧ | $^{28}$Trp—Val—Cys—Ala—Ala—Lys—Phe—Glu—Ser—Asn—Phe—Asn—Thr—Gln—Ala—Thr—Asn$^{44}$ $^{40}$Thr—Gln—Ala—Thr—Asn—Arg—Asn—Thr—Asp—Gly—Ser—Thr—Asp—Tyr—Gly—Ile—Leu—Gln—Ile—Asn—X |
| ⑨ | $^{45}$Arg—Asn—Thr—Asp—Gly—Ser—Thr—Asp—Tyr—Gly—Ile—Leu—Gln—Ile—Asn$^{59}$ $^{28}$Trp—Val—Cys—Ala—Ala—Lys—Phe—Glu—Ser—Asn—Phe—Asn—Thr—Gln—Ala—Thr—Asn—X |
| 10 | $^{1}$Lys—Val—Phe—Gly—Arg—Cys—Glu—Leu—Ala—Ala—Ala—Met—Lys—Arg—His—Gly—Leu—Asp—Asn$^{19}$ |
| 11 | $^{104}$Gly—Met—Asn—Ala—Trp—Val—Ala—Trp—Arg—Asn$^{113}$ |

TABLE 2-continued

| Peak numbers in FIG. 2 | Amino acid sequence of peptide fragment |
|---|---|
| 12 | $\overset{114}{\text{Arg}}$—Cys—Lys—Gly—Thr—Asp—Val—Gln—Ala—Trp—<br>Ile—Arg—Gly—Cys—Arg—$\overset{129}{\text{Leu}}$ |
| 13 | $\overset{66}{\text{Asp}}$—Gly—Arg—Thr—Pro—Gly—Ser—Arg—Asn—Leu—<br>Cys—Asn—Ile—Pro—Cys—Ser—Ala—Leu—Leu—Ser—<br>Ser—Asp—Ile—Thr—Ala—Ser—Val—$\overset{93}{\text{Asn}}$ |
| 14 | $\overset{1}{\text{Lys}}$—Val—Phe—Gly—Arg—Cys—Glu—Leu—Ala—Ala—<br>Ala—Met—Lys—Arg—His—Gly—Leu—Asp—Asn—Tyr—<br>Arg—Gly—Tyr—Ser—Leu—Gly—$\overset{27}{\text{Asn}}$ |
| 15 | $\overset{28}{\text{Trp}}$—Val—Cys—Ala—Ala—Lys—Phe—Glu—Ser—Asn—<br>Phe—Asn—Thr—Gln—Ala—Thr—Asn—Arg—Asn—Thr—X<br>$\overset{60}{\text{Ser}}$—Arg—Trp—Trp—Cys—Asn—Asp—Gly—Arg—Thr—<br>Pro—Gly—Ser—Arg—Asn—Leu—Cys—Asn—Ile—Pro—X<br>$\overset{114}{\text{Arg}}$—Cys—Lys—Gly—Thr—Asp—Val—Gln—Ala—Trp—<br>Ile—Arg—Gly—Cys—Arg—$\overset{129}{\text{Leu}}$ |
| 16 | $\overset{107}{\text{Ala}}$—Trp—Val—Ala—Trp—Arg—Asn—Arg—Cys—Lys—<br>Gly—Thr—Asp—Val—Gln—Ala—Trp—Ile—Arg—Gly—<br>Cys—Arg—$\overset{129}{\text{Leu}}$ |

Remarks: X shows unidentified fragment

The results showed that this enzyme cleaved only amide bonds on the C-terminal side of the L-asparagines contained in the soluble reduced lysozyme.

As described in detail above, this invention provides a method for the hydrolysis of the amide bonds on the C-terminal side of L-asparagine in peptide chains, and provides a reagent for use in the hydrolysis, and novel asparaginyl endopeptidase. This invention can be used in procedures indispensible to the structural analysis of proteins.

What we claim is:

1. A method for the hydrolysis of an amide bond on the C-terminal side of an L-asparagine characterized by the use of an asparaginyl endopeptidase which is specific for only an amide bond on the C-terminal side of an L-asparagine contained in a compound having a peptide chain and at least one amide bond on the C-terminal side of L-asparagine.

2. A composition for use in the hydrolysis of an amide bond on the C-terminal side of an L-asparagine, which comprises an enzymatically effective amount of an asparaginyl endopeptidase, which is specific for only an amide bond on the C-terminal side of an L-asparagine contained in a compound having a peptide chain and at least one amide bond on the C-terminal side of L-asparagine, in a suitable medium.

* * * * *